United States Patent [19]
Ricketts et al.

[11] 3,985,147
[45] Oct. 12, 1976

[54] DENTAL IMPLEMENT FOR REMOVING STAINS FROM TEETH

[76] Inventors: Craig M. Ricketts; Robert M. Ricketts, both of 1283 Rimmer Ave., Pacific Palisades, Calif. 90272

[22] Filed: Mar. 13, 1975

[21] Appl. No.: 558,127

[52] U.S. Cl. ..................................... 132/89; 32/50
[51] Int. Cl.[2] ........................................ A61C 15/00
[58] Field of Search................. 32/50, 58; 132/84 R, 132/84 A, 89

[56] References Cited
UNITED STATES PATENTS

| | | | |
|---|---|---|---|
| 1,784,986 | 12/1930 | Eisenberg | 132/89 |
| 2,030,910 | 2/1936 | Blair | 32/59 |
| 3,330,732 | 7/1967 | Muhler | 132/89 UX |
| 3,800,812 | 4/1974 | Jaffe | 132/89 |

FOREIGN PATENTS OR APPLICATIONS

| | | | |
|---|---|---|---|
| 827,837 | 1/1952 | Germany | 132/89 |
| 106,556 | 11/1899 | Germany | 32/58 |

OTHER PUBLICATIONS
"The Improved Carborundum Dental Goods" Cat., Revised issue–1937, Carborundum Co., pp. 3–7.

*Primary Examiner*—Jack Q. Lever
*Attorney, Agent, or Firm*—Keith D. Beecher

[57] ABSTRACT

A dental implement is provided for removing stains and plaques from the teeth, and which may also be used as a gum stimulator. The implement is in the form of an elongated handle which may, for example, have the configuration of any one of the standard types of tooth brush handles. The handles may, for example, have a round, square, triangular or other cross-section shape, and it may be made of plastic or other suitable material. A tip is mounted on one end of the handle which is made of hardened rubber, plastic, or other appropriate material, and which has embedded in it an abrasive material such as a carborundum particles, pumice, or the like. The tip may also contain fluoride compounds, if desired, to aid in the resistance of the teeth to decay. It also may contain an appropriate flavoring to make the operation more enjoyable to the user. The other end of the handle is shaped to have a pick and hoe configuration to aid in the removal of plaques from the surface of and between the teeth. These ends may be offered as individual units rather than a double-ended instrument.

7 Claims, 3 Drawing Figures

DENTAL IMPLEMENT FOR REMOVING STAINS FROM TEETH

BACKGROUND OF THE INVENTION

Dentists have recommended that the teeth be well brushed every day to remove food particles, and to keep the teeth clean and to maintain their good appearance. It has been found, however, that even with regular brushing of the teeth with a usual toothbrush and dentrifice, the teeth can still become stained and discolored, and they are still subject to the build-up of tartar, and to the formation of plaques on the surface of and between the teeth.

The purpose of the present invention is to provide an improved dental implement which can be used in the same manner as an ordinary toothbrush, and which is effective for the removal of stains, tarter and plaques from the teeth, and which also may be used as a gum stimulator.

DETAILED DESCRIPTION OF THE ILLUSTRATED EMBODIMENT

Figure 1:
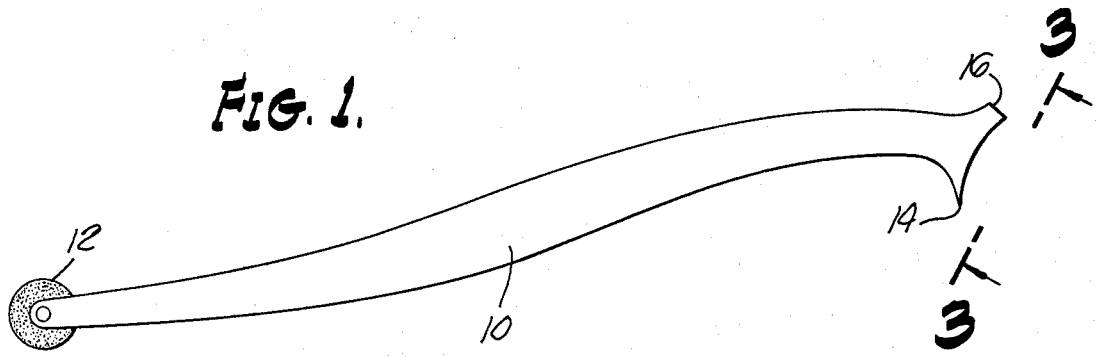
FIG. 1 is a side elevation of one embodiment of the invention.
Figure 2:
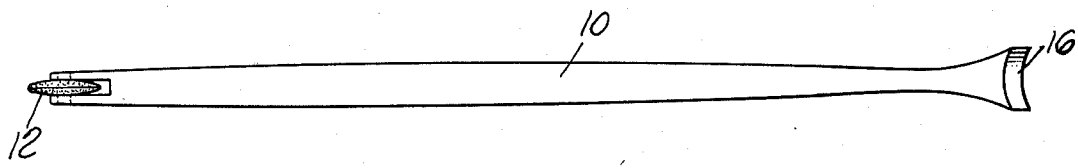
FIG. 2 is a side elevation of the embodiment of FIG. 1, turned through ninety degrees.
Figure 3:
FIG. 3 is an end view, taken along the line 3—3 of FIG. 1.

The dental implement shown in FIG. 1 has an elongated handle 10 which is bifurcated at one end to receive a disc-shaped insert 12. The insert 12 may be formed, for example, of hardened rubber, plastic, or other appropriate material. An abrasive material such as carborundum particles, pumice, or the like, is embedded in the insert 12. As mentioned above, the insert may also contain fluoride compounds for the preservation of the teeth, and/or an appropriate flavoring, if so desired.

The disc-shaped insert 12 is convenient in that it can be turned to a new angular position as it becomes worn. However, it is clear that the insert 12 may be any type of tip for the handle of any appropriate configuration.

The other end of the handle 10 is shaped to define a pick 14 which is convenient for the removal from behind the teeth of plaque formations between the teeth. The other end of the handle is also shaped to define a hoe 16 which forms a convenient scraper for tartar or plaque formation from the front surfaces of the teeth.

The implement may be easily manipulated by the dentist, or by the patient, to rub the surfaces of the teeth with the insert 12 in order to remove stains from the surfaces. Moreover, the implement may be easily used by the dentist, or by the patient, to remove tartar or plaques as described above, and to stimulate the gums.

While a particular embodiment of the invention has been shown and described, modifications may be made, and it is intended in the claims to cover the embodiments which come within the true spirit and scope of the invention.

What is claimed is:

1. A manually-operable dental implement comprising an elongated handle shaped to be grasped in the hand of a user to perform a stain removal operation on the teeth of a patient, and an abrasive-impregnated member mounted on one end of the handle for removing stains from the teeth, said member being in the form of a disc turnable about an axis traversing the longitudinal axis of the handle to different angular positions.

2. The dental implement defined in claim 1, in which said member is formed of hard fubber impregnated with an abrasive material.

3. The dental implement defined in claim 2, in which said abrasive material comprises particles of carborundum.

4. The dental implement defined in claim 1, in which the member contains fluoride compound to assist the teeth in their resistance to decay.

5. The dental implement defined in claim 1, in which the member includes a flavor ingredient to make the operation more enjoyable to the user.

6. The dental implement defined in claim 1, and which includes a pick and hoe member mounted on the other end of the handle.

7. The dental implement defined in claim 6, in which said pick and hoe member is integral with the handle.

* * * * *